United States Patent [19]
Haas

[11] Patent Number: 5,346,968
[45] Date of Patent: Sep. 13, 1994

[54] OLIGOSILOXANES AND REINFORCED THERMOPLASTIC AND CERAMIC MATERIALS OBTAINABLE THEREWITH

[75] Inventor: Karl-Heinz Haas, Frankenthal, Fed. Rep. of Germany

[73] Assignee: BASF Aktiengesellschaft, Ludwigshafen, Fed. Rep. of Germany

[21] Appl. No.: 159,707

[22] Filed: Dec. 1, 1993

Related U.S. Application Data

[63] Continuation of Ser. No. 944,744, Sep. 14, 1992, abandoned, which is a continuation of Ser. No. 682,294, Apr. 9, 1991, abandoned.

[30] Foreign Application Priority Data

Apr. 21, 1990 [DE] Fed. Rep. of Germany ....... 4012765

[51] Int. Cl.$^5$ ...................... C08L 79/08; C08L 77/00
[52] U.S. Cl. .................... 525/431; 525/446; 525/471; 525/474; 525/906; 528/39; 528/26; 528/17; 528/14; 528/38; 423/355; 556/457; 556/458
[58] Field of Search ....................... 528/39, 26, 17, 14, 528/38; 525/431, 446, 471, 474, 906; 556/457, 458; 423/325

[56] References Cited

U.S. PATENT DOCUMENTS

| | | | |
|---|---|---|---|
| 2,562,953 | 8/1951 | Rust | 528/39 |
| 3,829,529 | 8/1974 | Lengnick | 260/827 |
| 4,650,513 | 3/1987 | Becker et al. | 71/88 |
| 4,824,878 | 4/1989 | Sterzel | 523/307 |
| 5,030,699 | 7/1991 | Motoyama et al. | 525/477 |

FOREIGN PATENT DOCUMENTS

| | | | |
|---|---|---|---|
| 564796 | 10/1958 | Canada | 556/458 |
| 659083 | 3/1963 | Canada | 528/26 |

OTHER PUBLICATIONS

Colloid and Polymer Science 253 (1975), pp. 658–664.
J. Org. Chem. 5, 443–448 (1940).
Journ. of Non.-Crystalline Solids, 100, 174–193 (1988).

*Primary Examiner*—John C. Bleutge
*Assistant Examiner*—Margaret W. Glass
*Attorney, Agent, or Firm*—Keil & Weinkauf

[57] ABSTRACT

Oligosiloxanes of the formula I

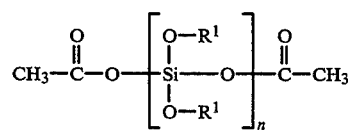

where
$R^1$ is a $C_1$–$C_4$-alkyl and
n is from 2 to 50, are chiefly used for fabricating fiber-reinforced composite and ceramic materials.

12 Claims, No Drawings

OLIGOSILOXANES AND REINFORCED THERMOPLASTIC AND CERAMIC MATERIALS OBTAINABLE THEREWITH

This application is a continuation of patent application Ser. No. 07/944,744, filed on Sep. 14, 1992 which is a continuation of patent application Ser. No. 07/682,294, filed on Apr. 9, 1991, both applications now abandoned.

The present invention relates to novel oligosiloxanes of the formula I

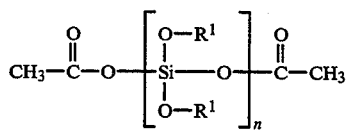

where
$R^1$ is $C_1$–$C_4$-alkyl and
n is from 2 to 50, preferably from 2 to 10.

The present invention also relates to a process for preparing these oligosiloxanes, to thermoplastic compositions which contain these compounds, to novel polysiloxanes, to a process for preparing these compounds and to thermoplastic compositions which contain these polysiloxanes.

The present invention also relates to composite materials formed from thermoplastic compositions and silicon dioxide reinforcing fibers, to these composite materials with adhesion promoters as further component, and to composite materials which additionally contain a finely divided ceramic material.

Additionally the present invention relates to shaped articles in a ceramic material reinforced with silicon dioxide fibers.

The composite materials formed from thermoplastics and inorganic fibers such as aluminum oxide and silicon dioxide are common knowledge.

The fibers in question can be prepared from the alkoxy compounds of the metals by in situ hydrolysis in solutions of the thermoplastics (DE-A-3,533,574 and 3,621,206).

However, the basically good reinforcing effect of these materials leaves something to be desired, presumably because the chain molecules are relatively short.

It is an object of the present invention to provide novel materials which can be used in particular for producing fiber-reinforced compositions.

We have found that this object is achieved by the oligosiloxanes I defined at the beginning and polysiloxanes III obtainable therefrom, processes for preparing same and thermoplastic compositions containing these compounds.

The present invention also provides composite materials formed from thermoplastic compositions and silicon dioxide reinforcing fibers, these composite materials with adhesion promoters as further component and with additional finely divided ceramic material and shaped ceramic articles obtainable therefrom.

In the oligosiloxane I according to the present invention, $R^1$ is $C_1$–$C_4$-alkyl such as methyl, n-propyl, isopropyl, n-butyl, isobutyl and tert-butyl but in particular ethyl.

The degree of polymerization n is from 2 to 10, preferably from 2 to 6.

The oligosiloxanes I are advantageously prepared by reacting oligomeric silicate esters of the formula II

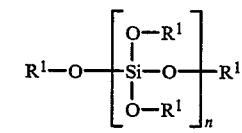

where n is as above, with acetic anhydride in a conventional manner (see for example J. Org. Chem. 5 (1940), 443–48).

The starting silicate esters II are known or obtainable by known methods (see for example Colloid+Polymer Sci. 253 (1975), 658–664).

The molar ratio of acetic anhydride to silicate ester II required for complete exchange of the end groups is at least 2:1, but preference is given to a molar ratio of 5:1, in particular of from 2.5:1 to 3:1.

As a process the procedure is in general to heat component II and the acetic anhydride to the reaction temperature and, after the reaction has ended, to distil off by-products and excess acetic anhydride.

In general, the reactions are carried out at from 50° to 140° C., preferably at from 120° to 140° C.; the corresponding reaction times are normally from 0.5 to 8, usually from 0.5 to 5, hours.

To speed up the reaction and to produce the reaction temperature required, it is advisable to carry out the process according to the present invention with the aid of a catalyst.

Suitable catalysts are mineral acids such as sulfuric acid, hydrochloric acid, phosphoric acid and nitric acid. Preference is given to using titania alkoxides, aluminum alkoxides and silicon tetrachloride. Particularly good results are obtained with perchloric acid.

In general, the catalysts are used in amounts of from 0.0005 to 0.1 mol %, preferably from 0.001 to 0.01 mol %, of the oligosiloxanes I.

If a catalyst is used, the reaction can in general be carried out at from 20° to 100° C., preferably at from 60° to 80° C., and the reaction time required also shortens to about 0.25-2 hours. Under these reaction conditions, the pendant (—O—$R^1$) groups are virtually not attacked.

Thus obtainable oligosiloxanes I can be converted into the linear polysiloxanes III according to the present invention by thermal polycondensation.

A very advantageous form of the thermal polycondensation in respect of the desired products to be formed from thermoplastic materials and silicon dioxide reinforcing fibers comprises heating a mixture of the thermoplastic and the oligosiloxanes I in an organic solvent.

Here the reaction temperatures are preferably from 200° to 350° C., in particular from 280° to 320° C., and the reaction times are normally from 1 to 30 minutes, usually from 3 to 10 minutes.

Suitable organic solvents are monomethoxyethanol, monoethoxymethanol, monomethoxyethanol, monoethoxymethanol, dimethoxyethanol, dimethyl sulfoxide, N-cyclohexylpyrrolidone, benzyl alcohol and N-methylpyrrolidone.

The conversion of the oligosiloxanes I into the polysiloxanes III is advantageously carried out in the presence of a free radical former as catalyst. Preferred catalysts are dibenzoyl peroxide, tert-butyl peroxobenzoate, tert-butyl peroxoacetate, dicumyl peroxide, cumyl hydroperoxide, di-tert-butyl peroxide, tert-butyl hydroperoxide and especially cumene hydroperoxide, aluminum alkoxides and dibutyltin diacetate, which in general are used in amounts of from 0.0001 to 1 mol %, preferably from 0.001 to 0.1 mol %, of the oligosiloxanes I.

If a catalyst is used, the reaction is customarily carried out at from 200° to 300° C., preferably at from 250° to 270° C., and the reaction times are in general from 1 to 10 minutes, preferably from 3 to 8 minutes.

The novel composite materials formed from thermoplastic compositions and silicon dioxide reinforcing fibers are prepared by acid hydrolysis and basic further condensation of polysiloxanes III dispersed in an organic solution of the thermoplastic composition and subsequent removal of volatiles.

Suitable thermoplastic materials are polyamides, e.g. nylon-6 and nylon-6.6, polyphenylene sulfones, polyphenylene ether sulfones, aromatic polyether imides, polyamide imides, aromatic polyether ketones and aromatic polyesters.

Advantageously, the hydrolysis reaction is catalyzed with a mineral acid such as sulfuric acid, hydrochloric acid, phosphoric acid or nitric acid, which are used in amounts of from 0.001 to 1 mol %, preferably from 0.05 to 0.5 mol %, of the oligosiloxanes I.

Further condensation is in general catalyzed with bases such as ammonia, $C_1$-$C_3$-alkylamines, ammonium fluoride, and also aluminum alkoxides or titanium alkoxides. These are used in amounts of from 0.01 to 1 mol %, preferably from 0.5 to 1 mol %, of the oligosiloxanes I.

In general, the hydrolysis and condensation reaction is carried out at from 200° to 350° C., preferably at from 280° to 350° C., and the corresponding reaction times range from 0.5 to 10 minutes, usually from 1 to 3 minutes.

For better force transmission between the fiber and thermoplastic material, it is possible to add an adhesion promoter.

Preferred adhesion promoters for apolar thermoplastics are methyltriethoxysilane, ethyltriethoxysilane, propyltriethoxysilane and phenyltriethoxysilane.

Preferred adhesion promoters for polar thermoplastics having acid functional groups are γ-aminopropyltrimethoxysilane, γ-aminopropyltriethoxysilane and N,N dimethylaminopropyltriethoxysilane.

Suitable adhesion promoters for polar thermoplastics having basic functional groups are preferably γ-cyanopropyltriethoxysilane or para-toluenesulfonyltrimethoxysilane, since their cyano and sulfonyl groups are converted by the hydrolysis into carboxyl and sulfo groups respectively.

The adhesion promoters are in general used in amounts of from 1 to 15 mol %, in particular from 5 to 10 mol %, of the oligosiloxanes I.

Owing to the limited thermostability of these compounds, the hydrolysis and condensation reaction is preferably carried out at from 220° to 280° C. if they are used.

As a process the general procedure is to add the oligosiloxanes I and the organic solvent to the thermoplastic material, which has been heated to the reaction temperature, then add first water and the acid catalyst and thereafter the basic catalyst and finally, after the adhesion promoter has been added, remove the volatile constituents by distillation.

To incorporate the adhesion-promoting functional groups into the silicon dioxide network, it is preferable to react the silicate esters II directly with the adhesion promoters.

The fiber-reinforced thermoplastic compositions thus obtainable have excellent mechanical properties and therefore are suitable for use as composite materials. A particular use of the fiber-reinforced thermoplastics is the manufacture of fiber-reinforced ceramic articles.

The process generally comprises adding a dispersion of a finely divided ceramic powder in an organic solvent to a hot mixture of a thermoplastic, silicon dioxide reinforcing fibers and adhesion promoter and then removing the solvent.

A suitable finely divided ceramic powder is fired or preferably unfired ceramic powder, obtainable in a conventional manner by the sol-gel process (D. Ulrich, Journ. of Non.-Cryst. Solids 100 (1988) 174).

The preferred ceramic material is the oxide ceramic material based on aluminum oxide, silicon dioxide, berylliun oxide, magnesium oxide, zirconium oxide or titanium dioxide. The solids content of the ceramic dispersion is preferably from 40 to 65% by volume. In general, the ceramic material is added to the thermoplastic in amounts of from 100 to 200% by weight, based on the oligosiloxanes I.

Preferred organic solvents are:
aliphatic polyethers such as diethylene glycol monobutyl ether, ethylene glycol monobutyl ether, diethylene glycol monoethyl ether and diethylene glycol diethyl ether;
amides such as N,N-dimethylacetamide, N-methylpyrrolidone and N-cyclohexylpyrrolidone, and
triphenyl phosphite, triphenyl phosphate and tricresyl phosphate.

The mixing of the ceramic dispersion with the fiber-reinforced thermoplastic material is carried out at 150°–300° C., preferably at 150°–250° C.

The further processing of the reaction mixture into fiber-reinforced ceramic articles is effected in a conventional manner, to be precise by granulating the compositions, removing excess solvent by drying, producing a shaped article from the granules, for example by injection molding, and then burning out the thermoplastic material and sintering the shaped article.

The burning-out of the thermoplastic is customarily carried out at from 400° to 700° C., in particular at from 500° to 600° C.

Owing to the heat treatment, the use of thermoplastic materials is restricted to those poisoners whose decomposition takes the forth of a depolymerization and hence does not leave any carbon residues.

Preferred polymers are polyoxymethylene and polyethylene.

All operations can be carried out at atmospheric pressure, but preference is given to working within the range from 2 to 100 bar.

The oligosiloxanes I and polysiloxanes III according to the present invention are preferably used for producing the novel compositions from thermoplastics and silicon dioxide reinforcing fibers with or without addition of adhesion promoters, which are used in the main as composite materials in the form of moldings, hollow articles, profiles, films, fibers or coatings and may be used for producing fiber-reinforced ceramic materials and shaped ceramic articles obtainable therefrom. Such articles are notable for high strength and toughness, low weight and simple processibility and therefore are used as construction materials in machine and apparatus construction and as substrate materials for integrated circuits.

The fiber-reinforced thermoplastic and ceramic materials obtained from the oligosiloxanes I and polysiloxanes III according to the present invention have excellent mechanical properties.

EXAMPLE 1

Preparation of 1,4-diacetoxytetra(diethoxy)siloxane

A mixture of 611 g g (1 mol) of 1,4-diethoxytetra(diethoxy)siloxane, 0.1 g (1 mmol) of perchloric acid and 204.2 g (2 mol) of acetic anhydride was heated at 70° C. for one hour, and then the volatile constituents of the reaction mixture were distilled off.

The residue was found by NMR to correspond to the title compound, which was obtained in a virtually quantitative yield. The SiOAc content of the product according to NMR spectroscopy was 20 mol %, based on the SiOEt groups.

EXAMPLE 2

Preparation of Ethoxypolysiloxane

A mixture of 639 g (1 mol) of 1,4-diacetoxytetra(diethoxy)siloxane and 2 1 of N-cyclohexylpyrrolidone was heated at 270° C. for 10 minutes in the presence of 3.5 g (0.01 mol) of dibutyltin diacetate.

The subsequent distillative removal of the volatiles and drying gave product III in a yield of 87% by weight.

EXAMPLE 3

Preparation of Fiber-Reinforced Polyphenylene Sulfone 6.39 kg (10 mol) of 1,4-diacetoxytetra(diethoxy)siloxane were added to a 300° C. mixture of 10 kg (0.3 mol) of polyphenylene sulfone and 1 1 of N-methylpyrrolidone in a twin-screw extruder. Addition of 3.5 g of dibutyltin diacetate, removal of the volatiles with distillation and drying gave the fiber-reinforced polyphenylene sulfone with a fiber content of 31% by weight.

EXAMPLE 4

Preparation of Fiber-Reinforced Polyphenylene Sulfone Having More Highly Crosslinked Chain Molecules A mixture of 14.5 kg of fiber-reinforced polyphenylene sulfone of Example 3 and 1.5 1 of N-methylpyrrolidone in a twin-screw extruder was admixed in a hot zone at 300° C. first with 2 1 of water, then with 8 ml of aqueous hydrochloric acid (32%) in 30 ml of N-methylpyrrolidone and, after a residence time of 1 minute, with 20 ml of aqueous ammonia (25%) in 70 ml of N-methylpyrrolidone. Then the volatiles were distilled off. The residue was dried to leave the fiber-reinforced polyphenylene sulfone having an SiO2 fiber content of 23% by weight.

The fiber-reinforced polyphenylene sulfone thus obtained has a better reinforcing effect than the product of Example 3 on account of its higher Si—O—Si network density.

EXAMPLE 5

Fabrication of a Ceramic Article 12.7 kg of a fiber-reinforced polyethylene obtained as described in Example 4 using diethylene glycol diethyl ether as solvent were heated to 200° C., a dispersion of 12 kg of aluminum oxide and 15 1 of diethylene glycol diethyl ether was added, and the volatiles were distilled off.

Then the material was granulated, and the dried granules were used to produce a round plate by injection molding. The polyethylene was burned out at 500° C. to leave the fiber-reinforced ceramic round plate. A further heat treatment at 1200° C. finally led to the $SiO_2$-fiber-reinforced $Al_2O_3$ ceramic. Owing to its high strength and excellent toughness, it is of particular importance for use as a construction material in machine and apparatus construction and as a substrate material for integrated circuits.

EXAMPLE 6

Production of Fiber-Reinforced Polyphenylene Sulfone Using an Adhesion Promoter

A mixture of 14.5 kg of fiber-reinforced polyphenylene sulfone of Example 3 and 1.5 1 of N-methylpyrrolidone in an extruder was admixed per hour in a hot zone at 280° C. with 66.3 g (0.3 mol) of 3-aminopropyltriethoxysilane as adhesion promoter dissolved in 50 ml of N-methylpyrrolidone. Following the addition of 2 1 of water, 8 ml of aqueous hydrochloric acid (32%) in 30 ml of N-methylpyrrolidone and 20 ml of aqueous ammonia (25%) dissolved in 100 ml of N-methylpyrrolidone, the volatiles were removed by distillation.

The granules were dried to leave a fiber-reinforced polyphenylene sulfone having an $SiO_2$ content of 25% by weight and exhibiting improved adhesion between fiber and matrix.

I claim:

1. A thermoplastic composition which comprises: an oligosiloxane of the formula

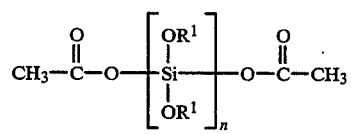

where $R^1$ is $C_1$-$C_4$-alkyl and n is from 2 to 50, and a polymer selected from the group consisting of polyamides, polyphenylene sulfones, polyphenylene ether sulfones, aromatic polyether imides, polyamide imides and aromatic polyether ketones.

2. The thermoplastic composition of claim 1, wherein $R^1$ is ethyl and n is 2 to 10.

3. A thermoplastic composition obtained by polymerizing an oligosiloxane of the formula

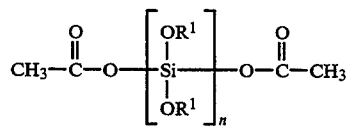

where $R^1$ is $C_1$-$C_4$-alkyl and n is from 2 to 50 in the presence of a thermoplastic material and thereafter adding to the composition an adhesion promoter selected from the group consisting of methyltriethoxysilane, propyltriethoxysilane, phenyltriethoxysilane, γ-aminopropyltrimethoxysilane, γ-aminopropyltriethoxysilane, γ-cyanopropyltriethoxysilane and N,N-dimethylaminopropyltriethoxysilane.

4. The thermoplastic composition of claim 3, wherein $R^1$ is ethyl and n is 2 to 10.

5. A thermoplastic composition obtained by (a) reacting an oligomeric silicate ester of the formula II

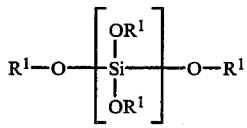

where $R^1$ is an alkyl of 1–4 carbons and n from 2 to 50, with an adhesion promoter selected from the group consisting of methyltriethoxysilane, ethyltriethoxysilane, propyltrithoxysilane, phenyltriethoxysilane, γ-aminopropyltrimethoxysilane, γ-aminopropyltriethoxysilane, γ-cyanopropyltriethoxysilane and N,N-dimethylaminopropyltriethoxysilane and thereafter reacting the product of step (a) with acetic anhydride in the presence of a catalyst selected from the group consisting of mineral acids, titanium alkoxides, aluminum alkoxides and silicon alkoxides to from reaction product (b) and subsequently polymerizing reaction product (b) in the presence of thermoplastic materials.

6. The thermoplastic composition of claim 5, wherein $R^1$ is ethyl and n is 2 to 10.

7. The composition of claim 5, wherein the adhesion promoter is selected from the group consisting of γ-aminopropyltrimethoxysilane, γ-aminopropyltriethoxysilane, N,N-dimethylaminopropyltriethoxysilane and γ-cyanopropyltriethoxysilane.

8. A process for preparing oligosiloxanes of the formula I

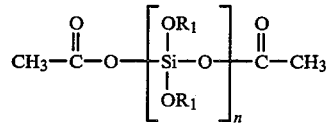

where $R^1$ is $C_1$–$C_4$-alkyl and n is from 2 to 50, which comprises: reacting a corresponding oligomeric silicate ester of the formula II

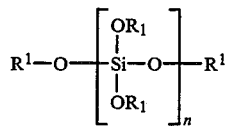

with acetic anhydride in the presence of a catalyst selected from the group consisting of mineral acids, titanium alkoxides, aluminum alkoxides and silicon tetrachloride.

9. The process of claim 8, wherein acetic anhydride is used in a molar excess of up to 5 moles per mole of silicate ester II.

10. The process of claim 8, wherein an amount of from 2.5 to 3 moles of acetic anhydride is used per mole of silicate ester II.

11. The process of claim 8, wherein the catalyst is perchloric acid.

12. The process of claim 8, wherein the catalyst is a titanium alkoxide, an aluminum alkoxide, or silicon tetrachloride.

* * * * *

UNITED STATES PATENT AND TRADEMARK OFFICE
CERTIFICATE OF CORRECTION

PATENT NO.: 5,346,968

DATED: September 13, 1994

INVENTOR(S): HAAS et al.

It is certified that error appears in the above-identified patent and that said Letters Patent is hereby corrected as shown below:

Column 6, claim 3, line 65, after "lane," insert --ethyltriethoxysilane--.

Column 7, claim 5, line 16, "propyltrithoxysilane" should read --propyltriethoxysilane--.

Column 7, claim 5, line 23, "from" should read --form--.

Signed and Sealed this

Fifteenth Day of November, 1994

Attest:

BRUCE LEHMAN

Attesting Officer

Commissioner of Patents and Trademarks